United States Patent [19]

Büchel et al.

[11] 3,987,180

[45] Oct. 19, 1976

[54] 1-PROPYL-IMIDAZOLYL ANTIMYCOTIC COMPOSITIONS AND METHODS OF TREATING MYCOSES

[75] Inventors: Karl Heinz Büchel; Wolfgang Krämer; Manfred Plempel, all of Wuppertal, Germany

[73] Assignee: Bayer Aktiengesellschaft, Germany

[22] Filed: Sept. 23, 1974

[21] Appl. No.: 508,685

[30] Foreign Application Priority Data

Oct. 5, 1973 Germany............................ 2350124

[52] U.S. Cl. .............................................. 424/273
[51] Int. Cl.² ....................................... A61K 31/415
[58] Field of Search ...................................... 424/273

[56] References Cited
UNITED STATES PATENTS 3,812,142  5/1974  Meiser et al. ....................... 424/269

*Primary Examiner*—Jerome D. Goldberg

[57] ABSTRACT

Pharmaceutical compositions are produced which comprise an antimycotically effective amount of a compound of the formula

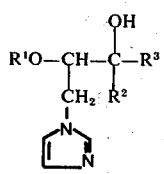

or a pharmaceutically acceptable non-toxic salt thereof wherein
 $R^1$ is an unsubstituted or substituted aryl moiety,
 $R^2$ is hydrogen, alkyl, alkenyl, cycloalkyl, unsubstituted or substituted aryl or unsubstituted or substituted aralkyl, and
 $R^3$ is hydrogen, alkyl or cycloalkyl,
provided that when $R^3$ is hydrogen, $R^2$ cannot be hydrogen, in combination with a pharmaceutically acceptable non-toxic inert diluent or carrier.

34 Claims, No Drawings

1-PROPYL-IMIDAZOLYL ANTIMYCOTIC COMPOSITIONS AND METHODS OF TREATING MYCOSES

The present invention is concerned with pharmaceutical compositions useful for treating mycoses in humans and animals, as well as to methods of treating mycoses in humans and animals. The active compounds of the present compositions and the active agents used in the method according to the present invention are 1-propyl-imidazolyl compounds.

More particularly, the present invention is concerned with pharmaceutical compositions useful for treating mycoses in humans and animals which comprises an antimycotically effective amount of a compound of the formula

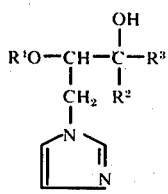

or a pharmaceutically acceptable non-toxic salt thereof wherein $R^1$ is an aryl moiety, especially aryl of 6 to 10 carbon atoms, and particularly phenyl or naphthyl, unsubstituted or substituted by 1 or more, preferably 1 to 3, and especially 1 or 2, of the same or different substituents selected from the group consisting of alkyl of 1 to 4 carbon atoms, halogen, haloalkyl of 1 or 2 carbon atoms in the alkyl moiety and 2 to 5 halogen moieties, alkoxy, especially alkoxy of 1 to 4 carbon atoms, haloalkoxy, especially of 1 to 4 carbon atoms in the alkoxy moiety and 3 to 5 halogen moieties, alkylthio, especially of 1 to 4 carbon atoms in the alkyl moiety, haloalkylthio, especially of 1 to 4 carbon atoms in the alkyl moiety and 3 to 5 halo moieties, alkylsulphonyl, especially of 1 to 4 carbon atoms in the alkyl moiety, nitro, amino, and phenyl;

$R^2$ is hydrogen; alkyl of 1 to 6 carbon atoms, especially of 1 to 4 carbon atoms; alkenyl of 2 to 6 carbon atoms; cycloalkyl of 5 to 7 carbon atoms; an aryl moiety, especially of 6 to 10 carbon atoms, particularly phenyl or naphthyl, unsubstituted or substituted by 1 or more, especially 1 to 3, and particularly 1 or 2, of the same or different substituents selected from the group consisting of alkyl of 1 to 4 carbon atoms, halogen, alkoxy, especially alkoxy of 1 to 4 carbon atoms, haloalkoxy, especially of 1 to 4 carbon atoms in the alkoxy moiety and 3 to 5 halogen moieties, alkylthio, especially of 1 to 4 carbon atoms in the alkyl moiety, haloalkylthio, especially of 1 to 4 carbon atoms in the alkyl moiety and 3 to 5 halo moieties, alkylsulphonyl, especially of 1 to 4 carbon atoms in the alkyl moiety, nitro, amino and phenyl; or an aralkylmoiety, especially of 6 to 10 carbon atoms in the aryl moiety and of 1 or 2 carbon atoms in the alkyl moiety, particularly benzyl, unsubstituted or substituted by 1 or more, especially 1 to 3, and particularly 1 or 2, of the same or different substituents selected from the group consisting of alkyl of 1 to 4 carbon atoms, halogen, alkoxy, especially alkoxy of 1 to 4 carbon atoms, haloalkoxy, especially of 1 to 4 carbon atoms in the alkoxy moiety and 3 to 5 halogen moieties, alkylthio, especially of 1 to 4 carbon atoms in the alkyl moiety, haloalkylthio, especially of 1 to 4 carbon atoms in the alkyl moiety and 3 to 5 halo moieties, alkylsulphonyl, especially of 1 to 4 carbon atoms in the alkyl moiety, nitro, amino and phenyl; and $R^3$ is hydrogen, alkyl of 1 to 6 carbon atoms, especially of 1 to 4 carbon atoms, or cycloalkyl of 5 to 7 carbon atoms, especially 5 or 6 carbon atoms;

provided that when $R^3$ is hydrogen, $R^2$ cannot be hydrogen.

When $R^2$ and/or $R^3$ is alkyl, the alkyl moieties include straight- as well as branched-chain alkyl moieties.

The following alkyl moieties are representative of those for $R^2$ and $R^3$: methyl, ethyl, n-propyl, i-propyl, n-butyl, i-butyl and t-butyl. A particularly preferred alkyl moiety for $R^2$ is methyl; and a particularly preferred alkyl moiety for $R^3$ is t-butyl.

When $R^3$ is cycloalkyl, cyclohexyl and cyclopentyl are preferred.

When $R^2$ is a substituted aryl or aralkyl moiety, the preferred substituents include straight- or branched-chain alkyl moieties of 1 to 4 carbon atoms, for example, methyl, ethyl, n-propyl, i-propyl, n-butyl, i-butyl and t-butyl, halogen, especially fluorine or chlorine, alkoxy, particularly of 1 or 2 carbon atoms such as methoxy and ethoxy, haloalkoxy such as trifluoromethoxy and pentafluoroethoxy, and haloalkylthio such as trifluoromethylthio, as well as nitro, amino and o- and p-phenyl.

When $R^1$ is substituted aryl, the preferred substituents include straight- or branched-chain alkyl of 1 to 4 carbon atoms such as methyl, ethyl, n-propyl, i-propyl, n-butyl, i-butyl or t-butyl, halogen, especially fluorine, chlorine and bromine, haloalkyl, especially wherein the halogen is fluorine and/or chlorine, for example, trifluoromethyl, haloalkoxy such as those wherein the halogen is fluorine and/or chlorine, such as trifluoromethoxy, difluorochloromethoxy and pentafluoroethoxy, alkoxy of 1 or 2 carbon atoms such as methoxy or ethoxy, haloalkylthio such as trifluoromethylthio or chlorodifluoromethylthio, as well as nitro, amino and o- and p-phenyl, or carbalkoxy of 1 to 4 carbon atoms in the alkoxy portion.

According to one embodiment of the present invention $R^1$ is phenyl, naphthyl or phenyl substituted by 1 to 3 substituents selected from the group consisting of fluorine, chlorine, bromine, methyl, tert.-butyl, or phenyl;

$R^2$ is hydrogen, alkyl of 1 to 4 carbon atoms, cycloalkyl of 5 or 6 carbon atoms, phenyl, naphthyl or benzyl; and $R^3$ is hydrogen, alkyl of 1 to 4 carbon atoms or cycloalkyl of 5 or 6 carbon atoms;

provided that when $R^3$ is hydrogen, $R^2$ cannot be hydrogen.

According to another embodiment of the present invention $R^1$ is phenyl unsubstituted or substituted by 1 or 2 substituents selected from the group consisting of chlorine, fluorine, bromine and methyl;

$R^2$ is hydrogen or alkyl of 1 to 4 carbon atoms; and $R^3$ is alkyl of 1 to 4 carbon atoms.

According to another embodiment of the present invention
R¹ is phenyl, chlorophenyl especially m-chlorophenyl or p-chlorophenyl, dichlorophenyl especially 2,4-dichlorophenyl, fluorophenyl, especially p-fluorophenyl, bromophenyl especially p-bromophenyl, or chloromethylphenyl especially 4-chloro-2-methylphenyl;
R² is hydrogen, methyl or t.-butyl; and
R³ is t.-butyl.

According to another embodiment of the present invention
R¹ is 4-chlorophenyl or 4-fluorophenyl;
R² is hydrogen or methyl; and
R³ is t.-butyl;
the hydrochloride salt thereof or the nitrate thereof.

According to another embodiment of the present invention
R¹ is phenyl unsubstituted or substituted by 1 or 2 members selected from the group consisting of chlorine, fluorine and methyl;
R² is hydrogen, methyl, cyclohexyl or benzyl; and
R³ is hydrogen or t.-butyl;
provided that when R³ is hydrogen, R² cannot be hydrogen.

According to another embodiment of the present invention
R¹ is phenyl, chlorophenyl, dichlorophenyl, fluorophenyl, or chloromethylphenyl;
R² is hydrogen, methyl, phenyl, chlorophenyl, or benzyl; and
R³ is hydrogen or t.-butyl;
provided that when R³ is hydrogen, R² cannot be hydrogen.

The 1-propyl-imidazolyl active compounds of the present invention are obtainable both in the erythro form and in the threo form. These forms can be separated by fractional crystallization or via their tartrates. However, the active compounds are predominantly in racemic form.

The erythro form and the threo form can be separated into their optical antipodes in accordance with techniques per se known. The present invention includes use of the active compounds in the form of optical isomers as well as racemates.

The pharmaceutically acceptable non-toxic salts of the above-referred-to compounds include salts formed with such acids as the hydrogen halide acids, phosphoric acid, nitric acid, monofunctional and bifunctional carboxylic acids, hydroxycarboxylic acids, for example, acetic, maleic acid, succinic acid, fumaric acid, tartaric acid, citric acid, salicylic acid, sorbic acid and lactic acid, and 1,5-naphalenedisulphonic acid. The hydrochlorides and nitrates are preferred salts.

Representative 1-propyl-imidazolyls according to the above invention include:
1-(imidazol-1-yl)-2-(4-chlorophenoxy)-3-hydroxy-4,4-dimethyl-pentane,
1-(imidazol-1-yl)-2-(3-chlorophenoxy)-3-hydroxy-4,4-dimethyl-pentane,
1-(imidazol-1-yl)-2-(2,4-dichlorophenoxy)-3-hydroxy-4,4-dimethyl-pentane,
1-(imidazol-1-yl)-2-(4-fluorophenoxy)-3-hydroxy-4,4-dimethyl-pentane,
1-(imidazol-1-yl)-2-phenoxy-3-hydroxy-4,4-dimethyl-pentane,
1-(imidazol-1-yl)-2-(4-chlorophenoxy)-3-hydroxy-3,4,4-trimethyl-pentane,
1-(imidazol-1-yl)-2-(2-chlorophenoxy)-3-hydroxy-4,4-dimethyl-pentane,
1-(imidazol-1-yl)-2-(4-chlorophenoxy)-3-hydroxy-3-benzyl-4,4-dimethyl-pentane,
1-(imidazol-1-yl)-2-(2-methyl-4-chlorophenoxy)-3-hydroxy-4,4-dimethyl-pentane and
1-(imidazol-1-yl)-2-phenoxy-3-cyclohexyl-3-hydroxypropane.

The 1-propyl imidazolyls referred to above may be prepared by reducing 1-propyl imidazoles of the formula

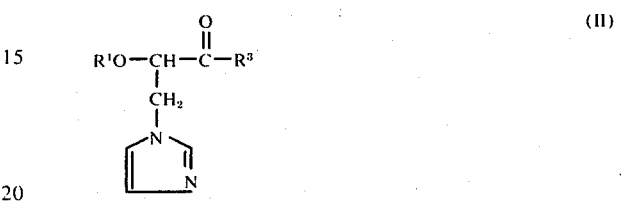

wherein R¹ and R² are as above defined, in accordance with techniques per se known, either with or without the simultaneous introduction of the R² moiety.

The reduction of the 1-propyl imidazoles II can be carried out (a) with hydrogen in the presence of a catalyst (for example, Raney nickel) and a polar solvent (for example, methanol) at a temperature of from 20° to 50° C or, (b) with aluminum isopropylate in the presence of an inert solvent at a temperature of from 20° to 120° C followed by hydrolysis, or (c) with a complex hydride (for example, sodium borohydride) in the presence of a polar solvent (for example, methanol) at a temperature of from 0° to 30° C, followed by a hydrolysis (for example, with aqueous hydrochloric acid), or (d) with formamidinesulphinic acid and an alkali metal hydroxide (for example, sodium hydroxide) in aqueous solution at a temperature of from 20° to about 100° C in the presence of a polar solvent (for example, ethanol).

The 1-propyl-imidazolyl compounds above described can also be prepared by subjecting compounds of formula II to reductive alkylation, cycloalkylation, aralkylation or arylation by means of Grignard reagents such as alkyl-, cycloalkyl-, aralkyl- or aryl-magnesium halides (preferably, iodides or bromides; for example, with methyl-magnesium iodide) in anhydrous diethyl ether at a temperature of from 20° to 80° C and subsequent hydrolysis, for example, with aqueous ammonium chloride solution. The compounds of the present invention thus obtained can be isolated in accordance with customary methods and, if desired, purified, for example, by distilling off any solvents, extracting the mixture with water and organic solvents, for example, ethyl acetate or methylene chloride, drying the organic phase and freeing it from the solvent. The residue thereby obtained can be further purified by recrystallization or salt formation.

The 1-propyl-imidazoles of formula I and their salts can be interconverted in any of the ways customary for the interconversion of free organic bases and their salts. For example, the base may be converted into a salt by dissolving the base in an ether (for example, diethyl ether) and adding the acid (for example, hydrogen chloride). The salt can be isolated in a known manner, for example, by filtration, and purified, if desired.

The 1-propyl-imidazoles of the formula II can be produced according to the process disclosed in German Offenlegungsschrift No. 2,242,454, British Application No. 40530/73, and corresponding United States application Ser. No. 390,042, filed 20/8/1973 [Le A 14 581-A] by:

a. reacting a compound of the formula

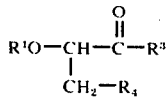 (III), wherein $R^1$ and $R^3$ are as above defined, and
$R^4$ is chlorine, bromine or hydroxyl, with imidazole, optionally in the presence of a highboiling solvent, for example, toluene, at 80° to 150° C;

or b. reacting a compound of the formula

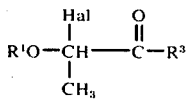 (IV), wherein $R^1$ and $R^3$ are as above defined, and
Hal is chlorine or bromine, with imidazole in a polar solvent, for example, acetonitrile, at a temperature of 60° to 120° C in the presence of acidbinding agents. The compounds of formula II can be isolated and purified in the usual manner.

The compounds of the formula III in which $R^4$ is hydroxyl, which are used as starting materials in methods (a) immediately above, are not previously known but can be prepared according to techniques per se known. For example, they are obtained when phenols or naphthols of the formula

 (V), wherein $R^1$ is as above defined, are condensed in a known manner with haloketones of the formula

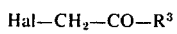 (VI), wherein $R^3$ is as above defined and
Hal is halogen (especially chlorine or bromine), and the resulting ketone of the formula

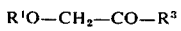 (VII), wherein $R^1$ and $R^3$ are as above defined, is reacted in accordance with know procedures in the presence of alkali (for example, aqueous sodium hydroxide solution) with formaldehyde or formaldehyde donors (for example, a 40 per cent strength aqueous formaldehyde solution) in an inert organic solvent (for example, ethanol) at an elevated temperature (for example, at the boiling point of the reaction mixture) and the desired product is isolated and purified in the usual manner.

The compounds of the formula III in which $R^4$ is halogen which are used as starting materials in method (a), immediately above, are not previously known but can be prepared according to techniques per se known, for example, by reacting the ether-ketone of formula VI, as explained above, with formaldehyde or a formaldehyde donor in the presence of alkali and subsequently reacting the resulting compound of the formula III in which $R^4$ is OH with a halogenating agent (such as thionyl chloride) in an inert, polar organic solvent (such as methylene chloride) at room temperature and isolating the desired end product in the usual manner and purifying it, if desired.

The halogen compounds of the formula IV used as starting materials in method (b) immediately above are not previously known but can be prepared according to tecniques per se known, for example, by reacting phenols or naphthols of the formula V in the usual manner with a haloketone of the formula

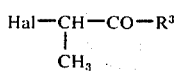 (VIII), wherein $R^3$ is as above defined and
Hal is halogen, preferably a chlorine or bromine.

The active hydrogen atom in the α-position is subsequently replaced by halogen in the usual manner, for example, by means of elementary bromine in carbon tetrachloride at 40° to 50° C. The desired product is isolated in a known manner and is optionally purified.

The active compounds of the present invention are useful for their antimicrobial and, particularly, their strong antimycotic effects. They have a broad antimycotic spectrum of activity, especially against dermatophytes and blastomyces, as well as biphase fungi, for example, against species of Candida (such as *Candida albicans*), species of Epidermophyton (such as *Epidermophyton floccosum*), species of Aspergillus (such as *Aspergillus niger*), species of Trichophyton (such as *Trichophyton mentagrophytes*), species of Microsporon (such as *Microsporon felineum*) and species of Penicillium (such as *Penicillium commune*), as well as biphase fungi such as *Histoplasma*, *Coccidioides* and *Sporotrichum*. The list of these microorganisms in no way represents a limitation of the microbes which can be combated and is only illustrative in character.

The following may be mentioned as examples of fields of indication in human medicine: dermatomycoses and systemic mycoses caused by *Trichophyton mentagrophytes* and other species of Trichophyton, species of Microsporon, *Epidermophyton floccosum*, blastomyces and biphase fungi as well as molds.

The following may be mentioned as examples of fields of indication in veterinary medicine: all dermatomycoses and systemic mycoses, especially those caused by the abovementioned pathogens.

The good microbiological activity of the active compounds of the invention is demonstrated by the following in vitro and in vivo experiments.

1. Determination of the antimycotic activity in vitro (series dilution test)

Description of the experiment

The nutrient substrate used was Sabourauds' milieu d'épreuve. The incubation temperature was 28° C and the incubation time was 24 to 96 hours. The test pathogens employed were *Candida albicans* and *Trichophyton mentagrophytes* as well as *Penicillin commune*, *Aspergillus niger* and *Microsporon felineum*, *Coccidiodes immitis*, *Torulopsis glabrata* and other less important pathogens.

Table A shows at what concentration growth was no longer detectable (MIC).

TABLE A

Minimum inhibitory concentration (MIC) in γ/ml of nutrient medium
In vitro test :

| Active compound | Example No. | Trichophyton mentagrophytes | Candida albicans | Penicillium commune | Aspergillus niger |
|---|---|---|---|---|---|
| 2-Cl-C₆H₄-O-CH(CH₂-Im)-CH(OH)-C(CH₃)₃ | 3 | 32 | 64* | >64 | — |
| 3-Cl-C₆H₄-O-CH(CH₂-Im)-CH(OH)-C(CH₃)₃ | 4 | >64 | 64⁺ | >64 | — |
| 2,4-Cl₂-C₆H₃-O-CH(CH₂-Im)-CH(OH)-C(CH₃)₃ | 5 | 4 | 64* | >64 | 64* |
| 4-F-C₆H₄-O-CH(CH₂-Im)-CH(OH)-C(CH₃)₃ | 6 | 64⁺ | 64⁺ | >64 | — |
| 4-Cl-C₆H₄-O-CH(CH₂-Im)-C(OH)(C(CH₃)₃)(CH₂-C₆H₅) | 2 | <1 | 64⁺ | >64 | >64 |
| 4-Cl-2-CH₃-C₆H₃-O-CH(CH₂-Im)-CH(OH)-C(CH₃)₃ | 7 | 4 | 64* | >64 | >64 |
| C₆H₅-O-CH(CH₂-Im)-CH(OH)-C(CH₃)₃ | 8 | 32 | 64* | >64 | — |
| 4-Cl-C₆H₄-O-CH(CH₂-Im)-C(OH)(CH₃)-C(CH₃)₃ | 9 | 8 | 64* | >64 | — |

TABLE A-continued

Minimum inhibitory concentration (MIC) in γ/ml of nutrient medium
In vitro test :

| Active compound | Example No. | Trichophyton mentagrophytes | Candida albicans | Penicillium commune | Aspergillus niger |
|---|---|---|---|---|---|
| 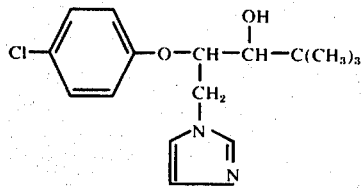 | 1 | 32 | 64* | >64 | — |

2. Antimycotic action of the compounds of the invention, in animal experiments.

a. Topical application against trichophytosis in guinea pigs.

A 1% strength solution of the active compounds in a dimethylsulphoxide/glycerol/water mixture (1:3:6) or in polyethylene glycol 400 was applied locally for 11 to 14 days after the trichophytosis (pathogen: *Trichophyton mentagrophytes*) had been produced experimentally.

The experimental results are reproduced in Table B.

Table B

Topical application against *trichophytosis* in guinea pigs.

| Compound from Example No. | Action |
|---|---|
| 7 | xx |
| 9 | xx |

Legend:
xx = healing of the infection inside 4–6 days after infection.

b. Oral administration against Quinckeanum trichophytosis in white mice

By using doses of 100 mg/kg of body weight, administered orally twice daily up to the eighth day of the infection, it was possible to suppress the development of the Quinckeanum infection in mice.

The result can be seen in Table C.

Table C

Oral administration against *Quinckeanum trichophytosis* in white mice

| Compound from Example No. | Action against Trichophyton quinckeanum |
|---|---|
| 7 | xx |
| 9 | xx |

Legend:
xx = fewer than 30% of the animals showed symptoms of the infection.

c. Oral Administration against candidosis in mice

Mice of type SPF-CF$_1$ were infected intravenously with $1-2 \times 10^6$ of logarithmically growing Candida cells which were suspended in physiological sodium chloride solution. One hour before and 7 hours after the infection, the animals were treated orally, in each case with 100 mg of the preparations/kg of body weight. Untreated animals died of the infection 3 to 6 days after the infection. The survival rate on the 6th day after infection was about 5% in the case of the untreated control animals.

The experimental results are summarized in Table D.

Table D

Oral administration against *candidosis* in mice

| Compound from Example No. | Action |
|---|---|
| 6 | ++++ |
| 7 | +++ |
| 9 | ++++ |
| 3 | ++ |

Legend, Table D:
++++ very good action = 90% survivors on the 6th day after infection
++++ good action = 80% survivors on the 6th day after infection
+++ action = 60–80% survivors on the 6th day after infection
++weak action = 50–60% survivors on the 6th day after infection The pharmaceutical compositions of the present invention contain a major or minor amount, e.g. 0.1 to 99.5%, preferably 0.5 to 95% of active ingredient as above defined in combination with a pharmaceutically acceptable non-toxic inert diluent or carrier, the carrier comprising one or more solid, semi-solid or liquid diluent, filler and formulation adjuvant which is non-toxic, inert and pharmaceutically acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three, four or more single doses or, alternatively, one half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once twice, three or four times a day. Other therapeutic agents can also be present.

Although the dosage and dosage regimen must in each case be carefully adjusted, utilizing sound professional judgement considering the age, weight and condition of the recipient, the route of administration and the nature and gravity of the illness, generally the dosage will be 10 mg/kg to 300 mg/kg, preferably from 50 mg/kg to 200 mg/kg, of body weight per day. In some instances a sufficient therapeutic effect can be obtained at a lower dose, while in others, a larger dose will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated for example by preparing a powder mixture, granulating or slugging, adding a lubricant and disintegrant and pressing into tablets. A powder mixture is prepared by mixing the compound, suitably comminuted, with a diluent or base as described above, optionally with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition to stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspension intended for subcutaneous, intramuscular or intravenous injection. These are prepared by suspending or dissolving a measured amount of the compound in a non-toxic liquid vehicle suitable for injection such as an aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Non-toxic salts and salt solutions can be added to render the injection isotonic. Stabilizers, preservatives and emulsifiers can also be added.

Rectal administration can be effected utilizing suppositories in which the compound is admixed with low-melting water-soluble or insoluble solids such as polyethylene glycol, cocoa butter, higher esters as for example myristyl palmitate, or mixtures thereof.

Topical administration can be effected utilizing solid dosage unit forms such as powders or liquid or semiliquid dosage unit forms such as solutions, suspensions, ointments, pastes, creams and gels. The powders are formulated utilizing such carriers as talc, bentonite, silicic acid, polyamide powder and the like. Liquid and semi-liquid formulations can utilize such carriers, in addition to those described above, as polyethylene glycol, vegetable and mineral oils, alcohols such as isopropanol and the like. Other excipients such as emulsifiers, preservatives, colorants, perfumes and the like can also be present. Formulations can also be administered as an aerosol, utilizing the usual propellants such as the chlorofluorohydrocarbons.

The preferred daily dose is 0.5g to 30 g, especially 2.5 g to 20 g, of active agent.

While the routes of administration include oral, parenteral (i.e., intramuscular, intraperitoneal, and intravenous), rectal, and topical, oral administration and topical application are particularly preferred.

The preferred pharmaceutical compositions are therefore those in a form suitable for oral administration such as tablets and suspensions and those suitable for topical application such as ointments.

The following Examples A and D describe by way of illustration only the preparation of pharmaceutical compositions and a medicament in dosage unit form according to the present invention.

EXAMPLE A: 1% strength solution for topical application

Sufficient polyethylene glycol 400 is added to 1 g of the compound from Example 4, while stirring and warming gently, to produce a total of 100 g of solution.

EXAMPLE B: 1% strength ointment for topical application 1 g of the compound from Example 4 is ground with 5 g of viscous liquid paraffin. Thereafter, sufficient ointment base consisting of liquid paraffin and polyethylene is added to produce a total of 100 g of ointment.

EXAMPLE C: 10% strength suspension elixir for oral administration

Sufficient vegetable oil is added to a mixture of 10 g of the active compound from Example 1 and 0.05 g of sodium saccharin and 2 g of colloidal silica and 0.2 g of peppermint oil to produce a total of 100 g of suspension elixir.

EXAMPLE D: Tablets, each containing 200 mg of active compound, for oral administration 2 g of compound from Example 4, 1 g of lactose and 0.3 g of maize starch are granulated with 0.1 g of maize starch paste. The mixture is beaten through a sieve of about 4 to 6 mm mesh width and dried. This dried mixture is homogenized through a sieve of 0.8 to 1 mm mesh width and then mixed with 0.15 g of starch and 0.02 g of magnesium stearate. The mixture thus obtained is pressed to give 10 tablets.

The following non-limitative examples more particularly illustrate the active compounds of the present invention:

EXAMPLE 1

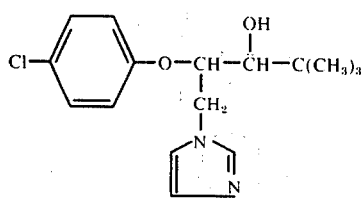

15.3 g (0.05 mol) of 1-(imidazol-1-yl)-2-(4-chlorophenoxy)-4,4-dimethyl-pentan-3-one are dissolved in 150 ml of methanol. 2.9 g (0.08 mol) of sodium borohydride are added thereto at 0° to 5° C and the mixture is stirred overnight at room temperature. It is then cautiously acidified with 10 ml of concentrated hydrochloric acid and the reaction mixture is again stirred overnight at room temperature and is poured into 250 ml of saturated sodium bicarbonate solution. After extraction with twice 100 ml of methylene chloride, the organic phase is washed with twice 100 ml of water and dried over sodium sulphate, and the solvent is distilled off under reduced pressure. The crystalline residue is boiled up with 100 ml of cyclohexane, filtered off hot and dried.

13.4 g (87% of theory) of 1-(imidazol-1-yl)-2-(4-chlorophenoxy)-3-hydroxy-4,4-dimethyl-pentane of melting point 163° to 170° C are obtained.

The starting compound is prepared as follows:

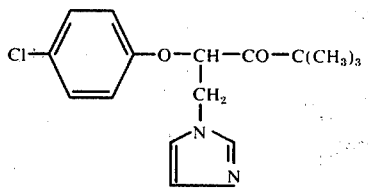

Method (a)

16.0 g(0.05 mol) of 2-(4-chlorophenoxy)-2-bromo-4,4-dimethyl-pentan-3-one in 120 ml of acetonitrile are heated with 12 g (0.207 mol) of imidazole for 12 hours to the boil under reflux. The solvent is then distilled off in vacuo until the mixture is almost reduced to dryness and 50 ml of ether and 50 ml of a saturated solution of hydrogen chloride in either are then added. The resulting oil is decanted off and boiled up three times with 50 ml of ether at a time, and the ether phase is decanted off. The oil which remains is taken up in 120 ml of methylene chloride, 50 ml of water and 20 g of solid sodium bicarbonate are added, the organic phase is separated off and the aqueous phase is extracted with twice 50 ml of methylene chloride. The combined organic phases are washed with twice 50 ml of water, dried over sodium sulphate and distilled in vacuo. The oil which remains is triturated with ligroin/petroleum ether, whereupon it crystallizes. After recrystallization from ligroin/petroleum ether, 2.6 g of 1-(imidazol-1-yl)-2-(4-chlorophenoxy)-4,4-dimethyl-pentan-3-one (representing 17% of theory) of melting point 68°–73° C are obtained.

The starting product, 2-(4-chlorophenoxy)-2-bromo-4,4-dimethyl-pentan-3-one, is obtained by bromination of 2-(4-chlorophenoxy)-4,4-dimethyl-pentan-3-one with elementary bromine in carbon tetrachloride at 40°–50° C; melting point: 95° C.

Method (b)

1-(Imidazol-1-yl)-2-(4-chlorophenoxy)-4,4-dimethylpentan-3-one can, however, also be prepared by dissolving 22.6 g (0.1 mol) of 1-(4-chlorophenoxy)-3,3-dimethyl-butan-2-one in 200 ml of ethanol and adding 200 g (0.24 mol) of 40 per cent strength formaldehyde solution followed by about 5 ml of 10% strength sodium hydroxide solution until the pH is 9. The reaction mixture is heated under reflux for 3 hours and the solvent is distilled off in vacuo. The resulting precipitate is filtered off and well rinsed with petroleum ether. The filtrate is concentrated in vacuo. An oil remains; this is crude 2-(4-chlorophenoxy)-1-hydroxy-4,4-dimethyl-pentan-3-one.

25.6 g (0.1 mol) of 2-(4-chlorophenoxy)-1-hydroxy-4,4-dimethyl-pentan-3-one are taken up in 200 ml of toluene, 10.2 g (0.14 mol) of imidazole are added dropwise and the reaction solution is boiled under a water separator for 3 hours. The solvent is then distilled off in vacuo, 100 ml of water are added to the resulting oil and the mixture is extracted with twice 100 ml of methylene chloride. The organic phase is washed with twice 50 ml of water and dried over sodium sulphate and the solvent is distilled off in vacuo. An oil is obtained, which is taken up in 50 ml of ether and mixed with 50 ml of ether saturated with dry hydrogen chloride. The solvent is distilled off in vacuo and the resulting oil is taken up in a mixture of 500 ml of ligroin and 300 ml of ethyl acetate and heated to the boil under reflux. After carefully decanting the resulting solution and cooling it, 16.8 g (49% of theory) of 1-imidazol-1-yl)-2-(4-chlorophenoxy)-3-hydroxy-4,4-dimethylpentane hydrochloride precipitate and are filtered off. The base can be obtained from this material in the usual manner, for example by dissolving in water, rendering alkaline and extraction with ether or ethyl acetate.

EXAMPLE 2

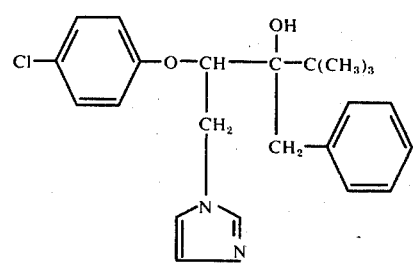

A solution of 10.7 g (0.1 mol) of benzyl chloride in 50 ml of anhydrous ether is added dropwise to a suspension of 2.4 g (0.1 mol) of magnesium filings in 30 ml of anhydrous benzene in such a way as to cause a slow but steady reaction. When all the benzyl chloride has been added, the reaction is allowed to continue for a further 30 minutes and a solution of 15.3 g (0.05 mol) of 1-(imidazol-1-yl)-2-(4-chlorophenoxy)-4,4-dimethyl-pentan-3-one in 250 ml of anhydrous tetrahydrofuran is then added dropwise. After heating for 15 hours under reflux, the solution is cooled and then stirred into 500 ml of aqueous 10 per cent strength ammonium chloride solution, and 50 ml of concentrated ammonia solution are added. After stirring for half an hour at room temperature, 100 ml of ethyl acetate are added and the organic phase is separated off, washed with four times 50 ml of water, dried over sodium sulphate and freed from the solvent in vacuo. The residue is boiled up with 100 ml of cyclohexane, filtered off hot and dried.

12.5 g (63% of theory) of 1-(imidazol-1-yl)-2-(4-chlorophenoxy)-3-benzyl-3-hydroxy-4,4-dimethyl-pentane of melting point 179° to 181° C are obtained.

The compounds of Examples 3 through 13 are set forth in Table 1 and prepared in analogous manner to that set forth above with respect to Examples 1 and 2.

Table 1

Compounds of the formula:

$$R^1O-CH(CH_2-\text{Im})-C(OH)(R^2)-R^3$$

where $CH_2$ is substituted with imidazol-1-yl (N).

| Example No. | $R^1$ | $R^2$ | $R^3$ | Melting Point, °C |
|---|---|---|---|---|
| 3 | 2-Cl-phenyl | H | $C(CH_3)_3$ | 162–163 |
| 4 | 3-Cl-phenyl | H | $C(CH_3)_3$ | 132–133 |
| 5 | 2,4-diCl-phenyl | H | $C(CH_3)_3$ | 198–202 |
| 6 | 4-F-phenyl | H | $C(CH_3)_3$ | 146–148 |
| 7 | 4-Cl-2-CH₃-phenyl | H | $C(CH_3)_3$ | 163–164 |
| 8 | phenyl | H | $C(CH_3)_3$ | 118 |
| 9 | 4-Cl-phenyl | $CH_3$ | $C(CH_3)_3$ | 155 |
| 10 | 4-Cl-phenyl | | phenyl (benzyl) H | 145–148° C |

Table 1-continued

Compounds of the formula:

$$R^1O-CH-C(OH)(R^3)-CH_2-N(imidazole), R^2$$

| Example No. | R¹ | R² | R³ | Melting Point, °C |
|---|---|---|---|---|
| 11 | phenyl | phenyl | H | 116° C |
| 12 | 4-Cl-phenyl | 4-Cl-phenyl | H | 160-165° C |
| 13 | 2,4-diCl-phenyl | 4-Cl-phenyl | H | 110-114° C |

What is claimed is:

1. A pharmaceutical composition for treating mycotic infections in humans and animals which comprises an antimycotically effective amount of a compound of the formula

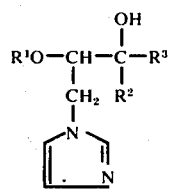

or a pharmaceutically acceptable non-toxic salt thereof wherein
R¹ is phenyl substituted by 1 to 3 halogen moieties or by 1 or 2 halogen moieties and 2 or 1 substituents selected from the group consisting of alkyl of 1 to 4 carbon atoms, haloalkyl of 1 or 2 carbon atoms in the alkyl moiety and 2 to 5 halo moieties, haloalkoxy of 1 to 4 carbon atoms in the alkoxy moiety and 3 to 5 halo moieties, and phenyl;
R² is hydrogen; alkyl of 1 to 6 carbon atoms; alkenyl of 2 to 6 carbon atoms; or cycloalkyl of 5 to 7 carbon atoms; and
R³ is hydrogen; alkyl of 1 to 6 carbon atoms; or cycloalkyl of 5 to 7 carbon atoms;
provided that when R³ is hydrogen, R² is not hydrogen; in combination with a pharmaceutically acceptable non-toxic inert diluent or carrier.

2. A composition according to claim 1 wherein
R¹ is phenyl substituted by 1 to 3 fluorine, chlorine or bromine moieties, or by 1 or 2 fluorine, chlorine or bromine moieties and 2 or 1 methyl, tert.-butyl, or phenyl moieties;
R² is hydrogen, alkyl of 1 to 4 carbon atoms or cycloalkyl of 5 or 6 carbon atoms; and
R³ is hydrogen, alkyl of 1 to 4 carbon atoms or cycloalkyl of 5 or 6 carbon atoms;
provided that when R³ is hydrogen, R² cannot be hydrogen.

3. A composition according to claim 1 wherein
R¹ is phenyl substituted by 1 or 2 chlorine, fluorine or bromine moieties, or by 1 chlorine, fluorine or bromine moiety and 1 methyl moiety;
R² is hydrogen or alkyl of 1 to 4 carbon atoms; and
R³ is alkyl of 1 to 4 carbon atoms.

4. A composition according to claim 1 wherein
R¹ is chlorophenyl, dichlorophenyl, fluorophenyl, bromophenyl or chloromethylphenyl;
R² is hydrogen, methyl or t.-butyl; and
R³ is t.-butyl.

5. A composition according to claim 1 wherein
R¹ is 4-chlorophenyl or 4-fluorophenyl;
R² is hydrogen or methyl; and
R³ is t.-butyl;
the hydrochloride salt thereof or the nitrate thereof.

6. A composition according to claim 1 wherein
R¹ is phenyl substituted by 1 or 2 chlorine or fluorine moieties or by 1 chlorine or fluorine moiety and 1 methyl moiety;
R² is hydrogen, methyl or cyclohexyl; and
R³ is hydrogen or t.-butyl;
provided that when R³ is hydrogen, R² cannot be hydrogen.

7. A composition according to claim 1 wherein
R¹ is chlorophenyl, dichlorophenyl, fluorophenyl, or chloromethylphenyl;
R² is hydrogen, methyl, or chlorophenyl; and
R³ is hydrogen or t.-butyl;
provided that when R³ is hydrogen, R² cannot be hydrogen.

8. A pharmaceutical composition according to claim 1 wherein the compound is

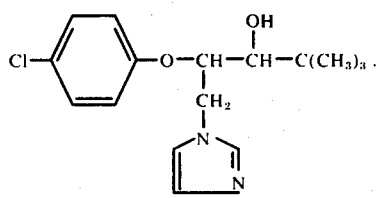

9. A pharmaceutical composition according to claim 1 wherein
R¹ is

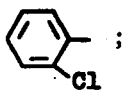

R² is hydrogen; and
R³ is C(CH₃)₃.

10. A pharmaceutical composition according to claim 1 wherein
R¹ is

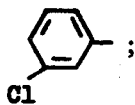

R² is hydrogen; and
R³ is C(CH₃)₃.

11. A pharmaceutical composition according to claim 1 wherein
R¹ is

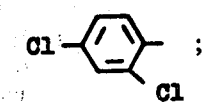

R² is hydrogen; and
R³ is C(CH₃)₃.

12. A pharmaceutical composition according to claim 1 wherein
R¹ is

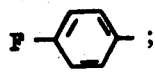

R² is hydrogen; and
R³ is C(CH₃)₃.

13. A pharmaceutical composition according to claim 1 wherein
R¹ is

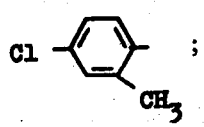

R² is hydrogen; and
R³ is C(CH₃)₃.

14. A pharmaceutical composition according to claim 1 wherein
R¹ is

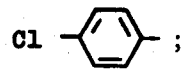

R² is CH₃; and
R³ is C(CH₃)₃.

15. A pharmaceutical composition according to claim 1 in oral administration form.

16. A pharmaceutical composition according to claim 1 in topical application form.

17. A method for treating mycoses in humans and animals which comprises administering to such human or animal an antimycotically effective amount of a compound of the formula

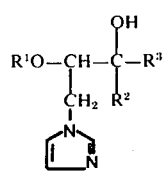

or a pharmaceutically acceptable non-toxic salt thereof wherein
R¹ is phenyl substituted by 1 to 3 halogen moieties or by 1 or 2 halogen moieties and 2 or 1 substituents selected from the group consisting of alkyl of 1 to 4 carbon atoms, haloalkyl of 1 or 2 carbon atoms in the alkyl moiety and 2 to 5 halo moieties, haloalkoxy of 1 to 4 carbon atoms in the alkoxy moiety and 3 to 5 halo moieties, and phenyl;
R² is hydrogen; alkyl of 1 to 6 carbon atoms; alkenyl of 2 to 6 carbon atoms; or cycloalkyl of 5 to 7 carbon atoms; and
R³ is hydrogen; alkyl of 1 to 6 carbon atoms; or cycloalkyl of 5 to 7 carbon atoms;
provided that when R³ is hydrogen, R² is not hydrogen.

18. A method according to claim 17 wherein
R¹ is phenyl substituted by 1 to 3 fluorine, chlorine or bromine moieties, or by 1 or 2 fluorine, chlorine or bromine moieties and 2 or 1 methyl, tert.-butyl, or phenyl moieties;
R² is hydrogen, alkyl of 1 to 4 carbon atoms or cycloalkyl of 5 or 6 carbon atoms; and
R³ is hydrogen, alkyl of 1 to 4 carbon atoms or cycloalkyl of 5 or 6 carbon atoms;
provided that when R³ is hydrogen, R² cannot be hydrogen.

19. A method according to claim 17 wherein
R¹ is phenyl substituted by 1 or 2 chlorine, fluorine or bromine moieties, or by 1 chlorine, fluorine or bromine moiety and 1 methyl moiety;
R² is hydrogen or alkyl of 1 to 4 carbon atoms; and
R³ is alkyl of 1 to 4 carbon atoms.

20. A method according to claim 17 wherein
R¹ is chlorophenyl, dichlorophenyl, fluorophenyl, bromophenyl or chloromethylphenyl;
R² is hydrogen, methyl or t.-butyl; and
R³ is t.-butyl.

21. A method according to claim 17 wherein
R¹ is 4-chlorophenyl or 4-fluorophenyl;
R² is hydrogen or methyl; and
R³ is t.-butyl;
the hydrochloride salt thereof or the nitrate thereof.

22. A method according to claim 17 wherein
R¹ is phenyl substituted by 1 or 2 chlorine or fluorine moieties or by 1 chlorine or fluorine moiety and 1 methyl moiety;
R² is hydrogen, methyl or cyclohexyl; and
R³ is hydrogen or t.-butyl;
provided that when R³ is hydrogen, R² cannot be hydrogen.

23. A method according to claim 17 wherein
R¹ is chlorophenyl, dichlorophenyl, fluorophenyl, or chloromethylphenyl;
R² is hydrogen, methyl, or chlorophenyl; and
R³ is hydrogen or t.-butyl;
provided that when R³ is hydrogen, R² cannot be hydrogen.

24. A method according to claim 17 wherein the compound is

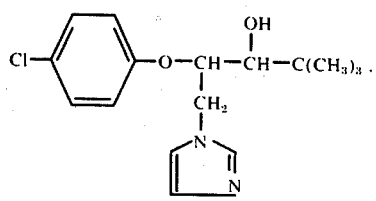

25. A method according to claim 17 wherein R¹ is

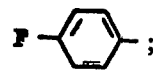

R² is hydrogen; and
R³ is C(CH₃)₃.

26. A method according to claim 17 wherein R¹ is

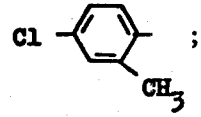

R² is hydrogen; and
R³ is C(CH₃)₃.

27. A method according to claim 17 wherein R¹ is

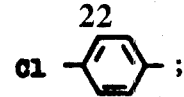

R² is CH₃; and
R³ is C(CH₃)₃.

28. A method according to claim 17 wherein R¹ is

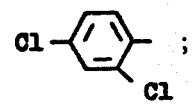

R² is hydrogen.
R³ is C(CH₃)₃.

29. A method according to claim 17 wherein R¹ is

F—⌬—;

R² is hydrogen; and
R³ is C(CH₃)₃.

30. A method according to claim 17 wherein R¹ is

Cl—⌬—CH₃ ;

R² is hydrogen; and
R³ is C(CH₃)₃.

31. A method according to claim 17 wherein the administration is oral.

32. A method according to claim 17 wherein the administration is by topical application.

33. A method according to claim 17 wherein the antimycotically effective amount is from 10 mg/kg to 300 mg/kg per day.

34. A method according to claim 17 wherein the antimycotically effective amount is from 50 mg/kg to 200 mg/kg per day.

* * * * *